(12) United States Patent
Qiao et al.

(10) Patent No.: US 7,183,119 B2
(45) Date of Patent: *Feb. 27, 2007

(54) METHOD FOR SENSITIVE DETECTION OF MULTIPLE BIOLOGICAL ANALYTES

(75) Inventors: Tiecheng A. Qiao, Webster, NY (US); Brian J. Kelley, Farmington, NY (US)

(73) Assignee: Eastman Kodak Company, Rochester, NY (US)

( * ) Notice: Subject to any disclaimer, the term of this patent is extended or adjusted under 35 U.S.C. 154(b) by 108 days.

This patent is subject to a terminal disclaimer.

(21) Appl. No.: 10/989,072

(22) Filed: Nov. 15, 2004

(65) Prior Publication Data

US 2006/0105352 A1 May 18, 2006

(51) Int. Cl.
*G01N 33/53* (2006.01)
*G01N 33/532* (2006.01)
*G01N 33/543* (2006.01)
*C07C 39/04* (2006.01)
*C09D 189/00* (2006.01)

(52) U.S. Cl. ............ 436/518; 436/524; 436/527; 436/544; 436/824; 435/7.1; 435/7.91; 435/7.97; 568/362; 530/812; 106/160.1

(58) Field of Classification Search ............ 436/518, 436/523, 524, 527, 544, 824; 435/7.1, 7.91, 435/7.97, 518, 7.9; 568/362; 530/812; 106/160.1
See application file for complete search history.

(56) References Cited

U.S. PATENT DOCUMENTS

| 4,782,023 A | 11/1988 | Anawis et al. |
|---|---|---|
| 4,962,029 A | 10/1990 | Levenson et al. |
| 5,182,376 A | 1/1993 | Edwards et al. |
| 5,650,324 A | 7/1997 | Gorman et al. |
| 5,776,714 A | 7/1998 | Snoke |
| 5,792,618 A | 8/1998 | Starkweather et al. |
| 5,981,180 A | 11/1999 | Chandler et al. |
| 5,989,842 A | 11/1999 | Schmidt et al. |
| 6,023,540 A | 2/2000 | Walt et al. |
| 6,162,610 A | 12/2000 | Bronstein et al. |
| 6,258,551 B1 * | 7/2001 | Neuenhofer et al. .......... 435/7.1 |
| 6,815,078 B2 * | 11/2004 | Qiao et al. ............... 428/478.2 |
| 2003/0068609 A1 | 4/2003 | Chari et al. |
| 2005/0019828 A1 * | 1/2005 | Qiao et al. ................... 435/7.1 |
| 2005/0158793 A1 * | 7/2005 | Muraoka et al. ............. 435/7.1 |

FOREIGN PATENT DOCUMENTS

WO     WO 90/11525     * 10/1990

OTHER PUBLICATIONS

Co-pending U.S. Appl. No. 10/988,920, Qiao et al., Method and system for sorting and separating particles.
Co-pending U.S. Appl. No. 10/989,062, Qiao et al., Method and system for nucleic acid detection.
M. Han, X. Gao, J.Z. Su and S. Nie, *Quantum-dot-tagged microbeads for multiplexed optical coding of biomolecules*, Nature Biotech. vol. 19, pp. 631-635 (2001).

* cited by examiner

*Primary Examiner*—Long V. Le
*Assistant Examiner*—Shafiqul Haq
(74) *Attorney, Agent, or Firm*—Lynne M. Blank (57) ABSTRACT

The present invention relates to a method of detecting biological analytes comprising suspending a target analyte in a suspending solution containing polymeric particles marked with a probe, wherein the probe has an affinity for said target analyte; adding recognition unit-peroxidase conjugate marker to the suspending solution; forming a complex of the target analyte, the polymeric particles marked with a probe, and the recognition unit-peroxidase conjugate marker; contacting a gelatin surface with the suspending solution; adding developer to the suspending solution in contact with the gelatin surface in the presence of phenol to attach the complex to the gelatin surface; washing the gelatin surface; and detecting the complex attached to the gelatin surface.

51 Claims, 7 Drawing Sheets

FIG. 5C 1,000 CELLS/mL

FIG. 5B 10,000 CELLS/mL

FIG. 5A 100,000 CELLS/mL

METHOD FOR SENSITIVE DETECTION OF MULTIPLE BIOLOGICAL ANALYTES

CROSS REFERENCE TO RELATED APPLICATIONS

Reference is made to commonly assigned, co-pending U.S. Patent Applications:

Ser. No. 10/988,920 by Qiao et al. filed of even date herewith entitled "Method And System For Sorting And Separating Particles"; and Ser. No. 10/989,062 by Qiao et al. filed of even date herewith entitled "Method And System For Nucleic Acid Detection", the disclosures of which are incorporated herein.

FIELD OF THE INVENTION

The present invention relates generally to the field of methods and devices for detection of multiple biological analytes, such as protein and bacteria analytes, and more specifically to methods and devices based on adherence of surface modified polymeric particles to gelatin surfaces for the detection and identification of biological analytes.

BACKGROUND OF THE INVENTION

Immonoassays, in which antibodies are used in various formats to detect analytes, play an important role in the fields of clinical diagnostics, environmental analysis and basic biological research. Many rapid methods for detecting protein analytes, bacterial analytes with high selectivity and sensitivity have been developed in the past years. These include radio-activity based immunoassay, chemiluminescence based immunoassay, magnetic based assay, fluorescence or colormetric based immunoassay. Many are commercially available, evaluated and validated under stringent requirement testing programs. Some rapid test systems incorporate more than one immunology-based technology into the test system to improve specificity and/or sensitivity. Immunology-based rapid assays already in existence can be further modified or incorporated into other systems to improve their performance, which obviates the need to create entirely new detection systems.

Array based immunoassay technologies for multianalytes detection has exploded since the introduction of DNA microarray technology in the early 90s. The technology that produces high-density arrays formed by spatially addressable synthesis of bioactive probes on a 2-dimensional solid support has greatly enhanced and simplified the process of biological research and development. The key to current microarray technology is deposition of a bioactive agent at a single spot on a microchip in a "spatially addressable" manner. An alternative approach to the spatially addressable method is the concept of using fluorescent dye-incorporated polymeric particles to produce biological multiplexed arrays. U.S. Pat. No. 5,981,180 discloses a method of using color coded particles in conjunction with flow cytometry to perform multiplexed biological assay. Microspheres conjugated with DNA or monoclonal antibody probes on their surfaces were dyed internally with various ratios of two distinct fluorescence dyes. Hundreds of "spectrally addressed" microspheres were allowed to react with a biological sample and the "liquid array" was analyzed by passing a single microsphere through a flow cytometry cell to decode sample information. U.S. Pat. No. 6,023,540 discloses the use of fiber-optic bundles with pre-etched microwells at distal ends to assemble dye loaded microspheres. The surface of each spectrally addressed microsphere was attached with a unique bioactive agent and thousands of microspheres carrying different bioactive probes combined to form "particles array" on pre-etched microwells of fiber optical bundles. More recently, a novel optically encoded microsphere approach was accomplished by using different sized zinc sulfide-capped cadmium selenide nanocrystals incorporated into microspheres (Nature Biotech. 19, 631–635, (2001)). Given the narrow band width demonstrated by these nanocrystals, this approach significantly expands the spectral barcoding capacity in microspheres.

Even though the "spectrally addressed microsphere" approach does provide an advantage in terms of its simplicity over the old fashioned "spatially addressable" approach in microarray making, there was still a need in the art to make the manufacture of biological microarrays less difficult and less expensive.

U.S. Ser. No. 09/942,241 provides a microarray that is less costly and easier to prepare than those previously disclosed because the support need not be modified. Nevertheless, the microspheres remain immobilized on the substrate. U.S. Ser. No. 09/942,241 provides a microarray comprising: a substrate coated with a composition comprising microspheres dispersed in a fluid containing a gelling agent or a precursor to a gelling agent, wherein the microspheres are immobilized at random positions on the substrate. The substrate is free of receptors designed to physically or chemically interact with the microspheres. That invention utilizes a unique coating composition and technology to prepare a microarray on a substrate that need not be pre-etched with microwells or pre-marked in any way with sites to attract the microspheres, as disclosed in the art.

PROBLEM TO BE SOLVED

There remains a need for array-based assays using polymeric particles in a manner are low cost and quick to manufacture, easy to use, and have high detection sensitivity.

SUMMARY OF THE INVENTION

The present invention relates to a method of detecting biological analytes comprising suspending a target analyte in a suspending solution containing polymeric particles marked with a probe, wherein the probe has an affinity for said target analyte; adding recognition unit-peroxidase conjugate marker to the suspending solution; forming a complex of the target analyte, the polymeric particles marked with a probe, and the recognition unit-peroxidase conjugate marker; contacting a gelatin surface with the suspending solution; adding developer to the suspending solution in contact with the gelatin surface in the presence of phenol to attach the complex to the gelatin surface; washing the gelatin surface; and detecting the complex attached to the gelatin surface.

ADVANTAGEOUS EFFECT OF THE INVENTION

The present invention includes several advantages, not all of which are incorporated in a single embodiment. The present invention provides a method for fast, simple, and inexpensive disease prognosis and diagnosis. The invention is particular useful for detecting biomarker proteins in urine

DETAILED DESCRIPTION OF THE INVENTION

The present invention discloses a novel method for multiplexing detection of multiple bioactive analytes. It offers advantages of easy-to-use, less expensive to manufacture as well as high selectivity and sensitivity.

This invention relates to a composition and method for detecting multiple biological analytes, e.g. nucleic acid, protein, and bacteria. It comprises a) a surface coated with gelatin; b) an aqueous solution containing a phenolic compound in which the suspected target analytes are suspended; c) a conjugate containing a peroxidase and a recognition unit which has high affinity to an identifiable sequence on the target analyte; d) a population of polymeric particles with a diameter no less than 0.5 micron that are surface modified with a probe with high affinity to the target analyte. The population of particles may further comprises sub-populations that are distinguishable through colors that are incorporated in the particle. The method of detection comprises 1) suspending the target analyte or analytes in an aqueous solution containing phenolic compound and the polymeric particles marked with ligands; 2) adding recognition unit-peroxidase conjugate to the suspension; 3) pouring the suspension onto a gelatin coated surface; 4) adding hydrogen peroxide to the suspension spread on the gelatin surface; 4) washing the gelatin surface; 5) detecting the presence of target analytes by measuring the number of particles that are attached to the surface.

This measurement may include determining the color of each sub-population of particles as well as counting the number of each sub-population of particles. The invention is particularly useful for detecting multiple biomarker proteins in urine and serum for disease diagnosis. It can be also useful for detecting pathogenic bacteria.

As used herein, the term "analyte" means a biological molecule whose presence in a sample and identity needs to be identified. Some common analytes for this invention include, but not limited to, proteins, enzymes, bacteria, virus.

The conjugate marker in this invention consists of at least two parts; 1) a recognition unit for the analye; 2) a peroxidase enzyme. The recognition unit recognizes the analyte in a specific manner and binds to the analyte strongly. Typically the recognition unit should have an affinity constant to the target analyte of no less than $10^{-6}$ $M^{-1}$. In one preferred embodiment of the invention, an antibody is used as recognition units. The antibody can be the same or different from the protein capture agent. In another preferred embodiment of the invention, the recognition unit is a nucleic acid. If a target analyte molecule can be pre-labeled with small molecule marker such as biotin and digoxigenin, then avidin and anti-digoxigenin antibody will be used as recognition unit.

The peroxidase enzyme, can be connected to the recognition unit covalently or non-covalently. The peroxidase enzyme, can be connected to the recognition unit covalently or non-covalently. The peroxidase-containing conjugate marker used in the practice of the present invention is capable of binding to either the specific binding ligand of interest or its corresponding receptor. The recognition unit may be a labeled analog of the specific binding ligand (such as labeled haptenic derivatives of the ligand). In sandwich assays, the labeled immunoreactant can be a labeled receptor for the ligand, or it can be a labeled molecule (such as a labeled anti-antibody) which binds to the receptor (such as an antibody).

By "peroxidase" in this application is meant any peroxidative substance (enzymatic or otherwise) which catalyzes the oxidation of a substrate, such as a leuco dye, in the presence of hydrogen peroxide or other oxidant to produce an appropriate signal. Microbial, fungal or plant peroxidases are preferred with horseradish peroxidase being most preferred.

The amount of a peroxidase-containing conjugate marker in an element of this invention can vary widely due to the amount of the other components used in the reaction and the suspected amount of particles in the test sample.

The peroxidase-containing conjugate markers useful in this invention is preferably a peroxidase-labeled hapten derivative of the ligand or a peroxidase-labeled antibody. However, a conjugate of avidin or another specific binding compound with peroxidase also can be used in the practice of this invention. Where the label is on a hapten, for example, it can be a peroxidase-labeled drug, hormone, protein, metabolite, chelate or haptenic derivative of any of these. Examples of such materials include, but are not limited to, peroxidase-labeled haptenic derivatives of digoxin, diphenylhydantoin, phenobarbital, C-reactive protein, a thyronine derivative such as thyroxine, carbamazepine or another analyte described above.

The preferred peroxidase for this invention is horseradish peroxidase. Horseradish peroxidase C (E.C.1.11.1.7) (HRP) is the major peroxidase isozyme isolated from the horseradish (*Armoracia rusticana*). It is a monomeric glycoprotein of 308 amino acids the polypeptide chain having a MW of 33,980 D. There are three neutral carbohydrate side chains and 4 disulphide bridges. The amino acid sequence of the mature protein has been determined. The presence of a pyrrolidonecarboxylyl amino terminus indicates that the protein is probably produced as a precursor form that is processed on secretion. The active form of the enzyme contains a hemin prosthetic group.

The enzyme is particularly stable and is amenable to crosslinking and derivitisation without excessive loss of activity. A further advantage it presents over other enzymatic markers is that some substrates for the enzyme give rise to electron dense products that allow correlation of peroxidase location with cellular ultrastructure using electron microscopy. In addition, horseradish peroxidase is electron dense itself by virtue of the Fe it contains and as a result can act as an E.M. marker in its own right. Particular applications have been found in immunochemistry, where peroxidase cross linked to immunoglobulin is widely used in both ELISA based assay systems and immunocytochemistry. Methods have been described that use either direct crosslinking of peroxidase to the immunoglobulin or indirect crosslinking of biotin labelled immunoglobulin to a streptavidin/horseradish peroxidase complex. Such streptavidin complexes have also found widespread application in nucleic acid hybridzsation methods where biotinylated probe sequences can be localized by sequential incubation with the streptavidin/peroxidase complex and a suitable chromogenic peroxidase substrate. The amino acid sequence of horseradish peroxidase is taught by Welinder, K. G. (Eur. J. Biochem. 96, 483–502 (1979)).

The recognition unit and the peroxidase enzyme can be covalently or non-covalently linked together to form the peroxidase-containing conjugate markers. The covalent conjugation of the recognition unit and the peroxidase enzyme can be performed using any of a number of known procedures, and many of such reagents are commercially available from a number of sources. Preparatory procedures include those described by Hermanson in "Bioconjugation Techniques" Academic Press 1996 and in U.S. Pat. No. 5,106,732 (Kondo et al).

A protein capture agent can be designed and chemically attached to the surface of the particle. The term "protein capture agent" means a molecule that can interact with proteins in high affinity and high specificity. Typically it is desirable to have an affinity binding constant between a protein capture agent and target protein greater than $10^6$ $M^{-1}$. A protein molecule consists of 20 amino acids that are connected in linear manner covalently. Some proteins can be further modified at selected amino acids through posttranslational processes that include phosphorylation and glycosylation. A protein molecule can be used as a protein capture agent. There are several classes of molecules that can be used as protein capture agents on a protein microarray. Antibodies are a class of naturally occurring protein molecules that are capable of binding targets with high affinity and specificity. The properties and protocols of using antibody can be found in "*Using Antibodies; A Laboratory Manual*", (Cold Spring Harbor Laboratory Press, by Ed Harlow and David Lane, Cold Spring Harbor, N.Y. 1999). Antigens can also be used as protein capture agents if antibodies are intended targets for detection. Protein scaffolds such as whole protein/enzyme or their fragments can be used as protein capture agents as well. Examples include phosphotases, kinases, proteases, oxidases, hydrolyases, cytokines, or synthetic peptides. Nucleic acid ligands can be used as protein capture agent molecules after in vitro selection and enrichment for their binding affinity and specificity to certain targets. The principle of such selection process can be found in *Science*, Vol. 249, 505–510, 1990 and *Nature*, Vol. 346, 818–822, 1990. U.S. Pat. No. 5,110,833 discloses an alternative class of synthetic molecules that can mimic antibody binding affinity and specificity and can be readily prepared by the so called Molecular Imprinting Polymer (MIP). This technology has been reviewed in *Chem. Rev.* Vol. 100, 2495–2504, (2000).

The attachment of a protein capture agent to the surface of particles can be performed according to the published procedures in the art (Bangs Laboratories, Inc, Technote #205). Some commonly used chemically reactive groups for protein capture agent attachment to the surface of particle may be, but are not necessarily limited to an aldehyde, epoxy, hydrazide, vinyl sulfone, succinimidyl ester, carbodiimide, maleimide, dithio, iodoacetyl, isocyanate, isothiocyanate, aziridine. Other functionalities which may allow for the attachment of other molecules through the use of a coupling agent or further chemical reactants include primary, secondary, or tertiary amines, thiols, or carboxylic acids. Preferably the reactive unit is a primary or secondary amine, a vinylsulfonyl, or a carboxylic acid. Specific polymers which can be used for this purpose may be selected from the set consisting of, but not necessarily limited to poly (propyleneimine) and polymers and copolymers of N-aminopropyl (meth)acrylamide and secondary amine derivatives thereof, N-aminoethyl (meth)acrylate and secondary amine forms thereof, diallyamine, vinylbenzylamine, vinylamine, (meth)acrylic acid, vinylbenzyl mercaptan, and hydroxyethyl(meth)acrylate. Preferably, the polymer is poly (vinylamine), poly(propyleneimine), or poly(N-aminopropyl methacrylamide), polyacrylic acid, or polymethacrylic acid.

The polymeric particles of the invention can be organic or inorganic in composition, having different shapes, such as curvilinear, spherical, donut shaped, elliptical, cubic, rod, etc. The invention discloses a polymeric particle based method with each particle in the system having a distinct signature that would distinguish the particle. Such a signature may be based on color, shape or size of the particle.

In a preferred embodiment of the invention, a colored particle is used to differentiate each type of particle. For particle based on color, the color may be derived from mixing three dyes representing the primary colors R, G, B to create thousands of distinguishable particles with distinct "color addresses" (unique RGB values, e.g. R=0, G=204, B=153).

The particles can be made with sites on their surfaces that are "active", meaning that at such sites physical or chemical interaction can occur readily between the particle and other molecules or compounds. As in the examples below, to the surface of each color coded particle may be attached a pre-synthesized oligonucleotide, a protein, an antibody, an antibody fragment, or other biological agents. Therefore, each color address can correspond to a specific bioactive probe. These particles may be mixed in equal amounts, or different amounts in a multiplex format.

A method for coloring a microparticle has been described by L. B. Bangs in "*Uniform Latex Particles;*" Seragen Diagnostics Inc. 1984, the disclosure of which is hereby incorporated by reference. Another approach to coloring a microparticle with dye is by covalently coupling one or more dyes to the surface of the microparticles. Examples for this approach can be found in U.S. Pat. Nos. 5,194,300 and 4,774,189, the disclosures of which are hereby incorporated by reference. Colorants and pigments can also be incorporated into microparticles using micro-encapsulation methods as described in U.S. Pat. Nos. 5,073,498 and 4,717,655, the disclosures of which are hereby incorporated by reference. These methods can be performed by anyone skilled in the art.

Suitable methods for preparing polymeric particles are emulsion polymerization, as described in "Emulsion Polymerization" by I. Piirma, Academic Press, New York (1982) or by limited coalescence as described by T. H. Whitesides and D. S. Ross in *J. Colloid Interface Science*, vol. 169, pages 48–59, (1985), the disclosures of which are hereby incorporated by reference. The particular polymer employed to make the particles or microparticles is usually a water immiscible synthetic polymer that may be colored, such as any amorphous water immiscible polymer. Examples of polymers that are useful include polystyrene, poly(methyl methacrylate) and poly(butyl acrylate). Copolymers such as a copolymer of styrene and butyl acrylate may also be used.

In a preferred embodiment of the invention, the microparticles have a mean diameter of between 1 and 100 microns. Preferably, the mean diameter will be between 2 and 30 microns. Most preferably, the mean diameter will be between 3 and 20 microns. Preferably these particles will be monodisperse or relatively monodisperse. By "monodisperse" it is meant that the coefficient of the particle size distribution (i.e. the standard deviation as a percentage of the mean) will be less than 20%. Preferably, the coefficient of variation will be less than 15%. Most preferably, the coefficient of variation will be less than 10%.

In process as described in FIG. 1, particle 4 only consists of one type of particle. However, in a process as described in FIG. 2, particle 4 can be a plurality of particles with each type of particle that can be distinguishable from the other from the unique color encoding the particle.

The target particles are suspended/in or covered with a suitable liquid. The probe-bearing particles may be brought in contact with the surface of the gelatin layer by covering the gelatin layer with an amount of liquid, in which the particles are suspended or contained. The particles are allowed to sediment or settle to the surface, either by gravity alone or by centrifugation of the entire support, as well as, the gelatin layer, or the slide or vessel or container or other member which comprises the support and gelatin layer, or by using any other suitable type of method for assisting or accelerating the sedimentation of particles, such as for example, by changing the ionic strength or the pH of the solution in which the particles are suspended by adding suitable salt solutions or buffer solutions, or by using electrophoresis, by attracting the particles to the surface using suitable electrical currents passed between the layer or the substrate and a suitable electrode immersed in the liquid, or by any other suitable method known in the art for accelerating or assisting the sedimentation of particles.

In cases in which the target particles are viable cells, the suspending liquid may typically be a physiological solution or medium adapted for maintaining the viability of the cells at least for the duration of the separation or sorting procedure or for longer time periods. For example, the liquid may be phosphate buffered saline (PBS), or any other suitable physiological solution, or similar medium, known in the art.

The suspension can be buffered with one or more typical buffer systems, including but not limited to, phosphate saline buffer, tris buffer, MES buffer, glycine buffer, and acetate buffer.

After the particles are bound with the target nucleic acid as well as the conjugate markers, the suspension containing the particles can be poured over a gelatin coated surface. Normally, gelatin is coated onto a support and gelation occurs through a process by which gelatin solutions or suspensions of gelatin and other materials form continuous three-dimensional networks that exhibit no steady state flow. This can occur in polymers by polymerization in the presence of polyfunctional monomers, by covalent cross-linking of a dissolved polymer that possesses reactive side chains and by secondary bonding, for example, hydrogen bonding, between polymer molecules in solution. Polymers such as gelatin exhibit thermal gelation which is of the latter type. The process of gelation or setting is characterized by a discontinuous rise in viscosity. (See, P. I. Rose, "The Theory of the Photographic Process", 4$^{th}$ Edition, T. H. James ed. pages 51 to 67).

The gelatin substrate described in this invention can either be coated as is on any solid support, or with one or a combination of multiple hardening agents mixed in the gel. The level of the hardening agent should be from 0 to 20 wt. %, and preferably 0.5 to 8 wt. %, of the total gelatin coated.

There are two types of gelatin: acid pretreated and alkaline pretreated. The preferred gelatin is alkaline pretreated gelatin from bovine bone marrow, but gelatin can also come from other sources.

Figure 3A:
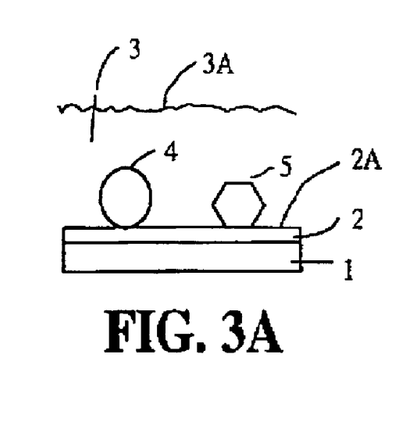
FIGS. 3A–3D are schematic diagrams illustrating the process of selectively attaching peroxidase labeled particles to gelatin coated surface.
Figure 3B:
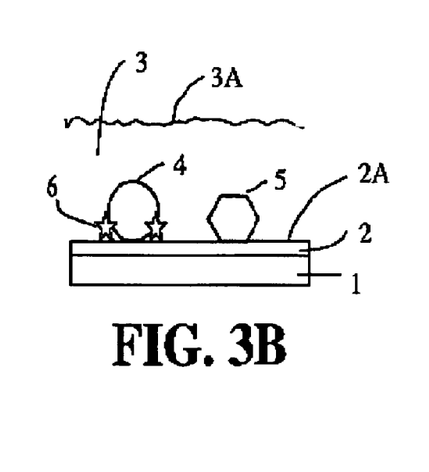

The gelatin surface for this invention can be flat, slightly curved, or stepped, and may include other supports having a surface which is not flat or is only partially flat. The gelatin is coated on a base called the "support" herein. Supports of choice for this invention can be organic, inorganic or biological. Some commonly used support materials include glass, quartz, plastics, metals, and semiconductors, but other substances or compositions may also be used. The support can be transparent or opaque, flexible or rigid. However, the material from which the support is made may also be opaque, or partially opaque, depending on the specific implementation or preferred embodiment of the present invention which is being used, and on the particular type of optical system used for implementing the invention, such as but not limited to, in optical systems using epi-illumination or reflected light. In some cases, the support can be a porous membrane e.g. nitrocellulose and polyvinylidene difluoride, and the gelatin can be deposited onto the membrane by physical adsorption. FIG. 3A shows a support 1 coated with a layer of gelatin 2. The support may be a part of a suitable member, such as a microscope slide, a Petri dish, an open container or vessel, or a covered container or vessel, or the like, depending on the specific implementation or preferred embodiment of the invention used.

Coating methods are broadly described by Edward Cohen and Edgar B. Gutoff in Chapter 1 of "Modern Coating And Drying Technology", (Interfacial Engineering Series; v.1), (1992), VCH Publishers Inc., New York, N.Y. In general, a fluid coating composition contains a binder, a solvent to dissolve or suspend the components, and optional additives such as surfactants, dispersants, plasticizers, biocides, cross-linking agents for toughness and insolubility, and conductive materials to minimize static buildup. All the components are mixed and dissolved or dispersed, and the coating fluid is sent to an applicator where it is applied to a substrate by one of several coating techniques. Heat is then applied to the coating to evaporate the solvent and produce the desired film, or the coating is solidified by the action of ultraviolet radiation or an electron beam.

The most suitable coating method—including the coating speed—will depend on the quality and functionality desired and the materials being used, e.g., the substrate, the solvent, weight and viscosity of the coating, etc. For a single layer format, suitable coating methods may include dip coating, rod coating, knife coating, blade coating, air knife coating, gravure coating, forward and reverse roll coating, and slot and extrusion coating.

Coating speed can also be an important determinant in the choice of coating method. Although most methods can be used at low speeds, and all methods have a limiting upper speed, some work better at higher speeds. Curtain coating requires a minimum flow to maintain the integrity of the curtain. Therefore, this method is limited to higher speeds if a thin coating is to be obtained. In slide coating of multiple layers, interfacial instabilities are more likely to occur on the slide when the layers are very thin. Higher speeds, with their higher flows and thicker layers on the slide, tend to avoid these instabilities. See, p. 12, "Modern Coating and Drying Technology", supra.

The gelatin has a laydown of 0.2 to 100 grams per square meter; preferably 10 to 50 grams per square meter.

Any well known coating method, such as particle coating or curtain coating, can be used to prepare the gelatin substrate. The gelatin could be coated with any other coating aids such as surfactants and thickeners to adjust its physical property. The gelatin used in the invention may be chemically modified either before, during or after the coating process to create more chemical functionalities that can react or interact with biologically active molecules or assemblies intended to be attached on this substrate.

The developer contains 1) a phenolic compound and 2) hydrogen peroxide. When the developer is added to the suspension solution containing the peroxidase-containing conjugate marker, a substance is formed in the vicinity of the particle 4 by the development. This substance binds or adheres the settled particles which are in contact with the gelatin surface 2A to the gelatin surface. Thus, the particle 4 adheres to or becomes effectively attached to the gelatin layer 2. In contrast to the particle 4 which becomes attached to the gelatin layer 2, the particle 5 is not attached to the gelatin layer 2 because the region of the layer 2 which underlies the particle 5 does not produce any substance 6.

The developer for this invention can be any hydrogen peroxide containing solution. The developer can be aqueous or non-aqueous, buffered or non-buffered. The concentration of hydrogen peroxide in the developer can be from 0.01% (w/v) to 10% (w/v).

The developer must function in the presence of at least one phenolic compound. The phenolic compound may be included in the suspension solution or added to the suspension solution after the suspension is poured over gelatin surface. The phenolic compound may be added in its own solution. The phenol must be added prior to or simultaneously with the hydrogen peroxide.

The phenolic compound is represented by the following general formula:

where R1, R2, R3, R4, R5 may be the same or different and may be hydrogen, a substituted or unsubstituted linear or branched alkyl group of 1 to 10 carbon atoms (such as methyl, ethyl, n-propyl, isopropyl, t-butyl, hexyl, decyl, benzyl, methoxymethyl, hydroxyethyl, ethyleneoxy, iso-butyl, and n-butyl), a substituted or unsubstituted aryl group of 6 to 14 carbon atoms (such as phenyl, naphthyl, anthryl, tolyl, xylyl, 3-methoxyphenyl, 4-chlorophenyl, 4-carbomethoxyphenyl and 4-cyanphenyl), a substituted or unsubstituted cycloalkyl group of 5 to 14 carbon atoms such as cyclopentyl, cyclohexyl, and cyclooctyl), a substituted or unsubstituted heterocyclic group (such as pyridyl, pyrimidinyl and furanyl), or a solubilizing group, or a halogen atom of fluoride, chloride, bromide, iodide. Preferably, at least one of the R groups is or contains a solubilizing substituent that is generally negatively charged such as an ionized acidic group. Examples of these solubilizing groups include, but are not limited to, carboxylic acid, sulfonic acid, phosphonic acid, sulfonamide, and hydroxy groups (and their corresponding salts), other solubilizing substituents which may be present on one or more R groups are polyethylenoxy, amino groups and others readily apparent to one skilled in the art. R1 and R2, and R3 and R4, may be joined by sufficient number of carbon, nitrogen, and sulfur atoms to form, independently, a five or six-member ring.

Representative phenolic compounds useful in the present invention are illustrated by the following structures:

The invention may be better understood by review of the Figures. Two different particles 4 and 5, as prepared from the processes of FIG. 1 and FIG. 2, are illustrated as being in contact with the surface 2A of the gelatin layer 2. The particle 4 contains a probe-analyte complex on its surface with peroxidase conjugate bound to the complex. In contrast, particle 5 represents particles that do not form any surface complexes, thus, no peroxidase conjugate bound to its surface. Even though only one particle 4 is shown in the Figure, it is understood that there are more one particle to be present in the method.

The non-adhered particle 5 may now be removed by suitably washing the gelatin layer 2 with a suitable washing liquid applied to the gelatin layer 2 while the adhered particle 4 remains attached to the layer 2. The layer 2 may be washed by additional amounts of a liquid having the same composition as the liquid 3 (preferably without the developer, to minimize the time of exposure of the particles to the developer). Alternatively, the washing may be accomplished by a liquid having a different composition than the liquid 3. The washing step washes the surface 2A of the layer 2, carries away the particle 5 and leaves behind the particle 4 adhered to the layer 2.

Figure 3C:
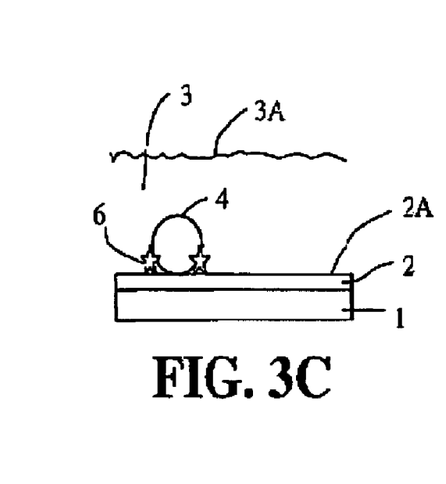

FIG. 3C illustrates the layer 2 and the particle 4 adhering to the gelatin surface 2A after the washing. The particle 5 is not illustrated in FIG. 3 C since it has been washed away by the washing step. The washing liquid or fluid (not shown)

including the particle 5 (not shown) may be collected for further utilization. Alternatively, the washing fluid may be discarded.

Figure 3D:
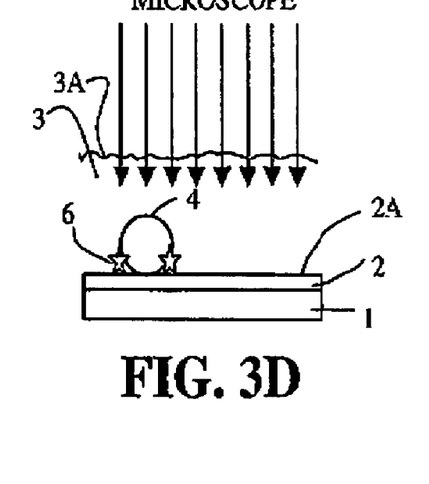

The washing conditions may have to be suitably adapted to ensure a good separation of the particles. Thus, the washing parameters, such as but not limited to, the composition of the washing fluid, the total amount or volume of the washing fluid used, the temperature of the washing fluid, the washing rate or flow rate of the washing fluid (expressed as the volume of washing fluid per time unit), the degree of turbulence in the washing fluid, and other washing parameters, may have to be controlled to ensure that all or most of the non-adhering particles (such as for example the particle 5 of FIG. 3B) will be removed from the gelatin layer 2 in the washing step. The concentration of target nucleic acid molecule is proportional to the number of particles attached to the gelatin surface, and such number can be quantified by simply counting the number of particle on the surface or by an automatic imaging method to analyze the number of particles on the surface. FIG. 3D shows a possible scheme where particle 4 can be visually detected under a microscope either with the liquid or without the liquid.

In accordance with one preferred embodiment of the present invention, the identification of the particle may be visually performed. For example, the support may be a part of a microscope slide (not shown in FIGS. 1A–1F), which is visually inspected using an appropriate microscope (not shown), or other suitable microscopy devices. The user of the microscope visually observes the particles and visually identifies the particles. Particles may be differentiated with respect to one or more property, to make them uniquely observable and countable, so that multiple particles may be detected at the same time.

The number of particles attached to the gelatin surface can be quantified by simply counting the number of particle on the surface or by an automatic imaging method to analyze the number of particles on the surface. In one identification scheme, particles can be visually detected under a microscope either with the liquid or without the liquid. The user of the microscope visually observes the particles 4 and 5 and visually identifies the particle 4 based on one or more of the different property differences between the particle 4 and the particle 5.

It is further noted that, while the optical system or microscope used for implementing some preferred embodiments of the present invention may use trans-illumination of the particles 4 and 5, or of other particles (not shown) which are to be analyzed, other methods of visualization or different methods of illumination may be used for visualizing and identifying the particles to be identified. For example, among the methods and techniques which may be used to visualize and/or identify or distinguish different particles are dark field illumination, epi-illumination, phase-contrast microscopy, differential interference contrast microscopy (DIC), polarization microscopy, multi-spectral or hyper-spectral microscopy involving the acquisition and analysis of pixel level spectrogram data as is known in the art, and any other suitable microscopy methods known in the art which may be adapted for use with the methods of the present invention.

Preferably, overlap of the particles should be avoided by proper adjustment of number of the particles to avoid or minimize the adhering of the "wrong" particles to the gelatin surface. The number of the particles is preferably optimized to avoid such undesirable adhering of particles. However, the particle number should be sufficiently high to allow the practical identification of the particles. Thus, the actual initial number of particles in the fluid suspension applied to the gelatin layer 2 may be a compromise which practically avoids contaminating undesired particles, while still ensuring high yield of the required particles to be identified. The initial number of particles may also depend on the type and morphological parameters of the particles, and on other factors. For certain applications in which a single particle, or very few particles is sufficient, a very low initial number of particles may be utilized in implementing the method of the present invention.

Figure 7A:
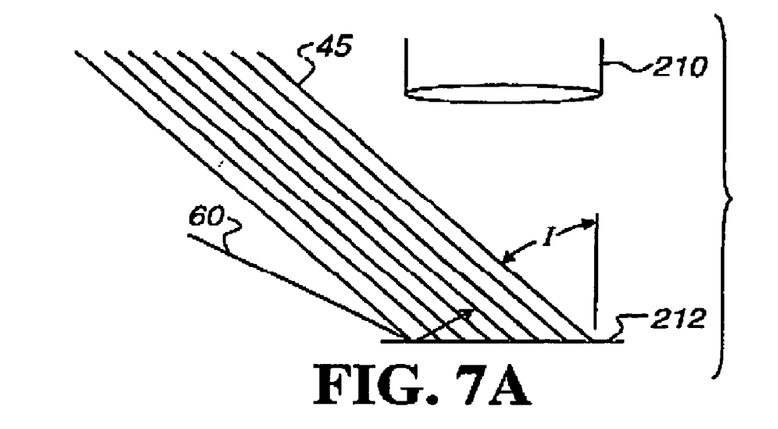
FIGS. 7A–7C illustrate an imaging system utilizing luminescent imaging/detection to analyze the colored particle.
Figure 7B:
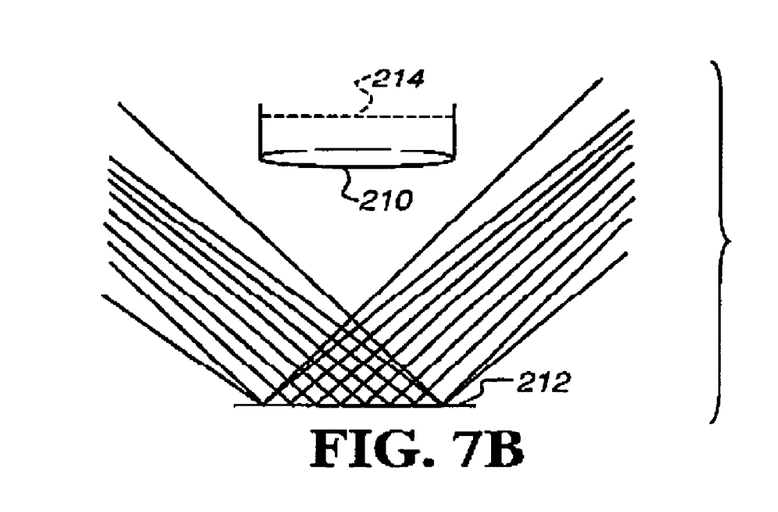
Figure 7C:
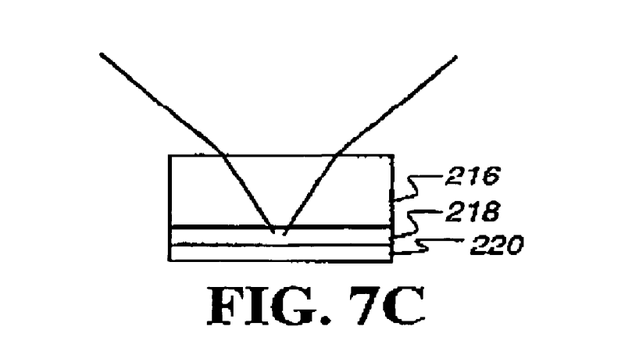

It is noted that there exist many possible ways to design an imaging system to analyze the colored particle, one such possible design for the invention is now described in reference to FIGS. 7A–7C, which are schematic diagrams illustrating the design principle and detection method of the invention in accordance with one preferred embodiment of the present invention. It is assumed that both absorbance color signals based on light adsorbing dyes as well as fluorescence color signals based on fluorescent dyes can be used to encode the particles of the invention. The most accommodating approach to obtain image data from a reporting flat object is full-frame image capture. The most important physical aspects of the image capture system is the balance between efficient light collection, optical resolution and effective illumination of the object and the balanced system must accommodate luminescent, fluorescent and absorbance modes of optical reporting. Further, the system must do so without significant movement of the object of interest and the imaging data must support the necessary measures relating to subsequent analysis. The design solutions to many of these requirements are well known to practitioners of the art; however, the system design to accommodate all requirements into a single practical solution requires invention.

A rational approach to design is to adhere to the most important dictates of the modes of imaging/detection: luminescent, fluorescent and absorbance. The design principles are illustrated in FIGS. 7A, 7B and 7C. FIG. 7A shows a lens 210 and object plane 212. FIG. 7B shows lens 210, object plane 212, and filter 214. FIG. 7C shows optical platen 216, aqueous layer 218, and object 220 on a mirror support.

The chief requirement of luminescent imaging/detection is efficient light detection, influenced by both collection and photometric integration. Efficient light collection requires a lens of large numerical aperture whose diameter is approximately the size of the field of view and positioned at a working distance that is close to the object. Practical solutions and cost lead to the solution illustrated in FIG. 7A, wherein an optical system specification of a lens 210 approximately f2 (lens diameter about half the working distance between lens 210 and object plane 212) is represented. Photometric integration requires a well-implemented sensor having sufficient dynamic range to generate a signal/noise ratio appropriate to support analysis. In practice, an integrated, cooled CCD sensor of 12-bits resolution and a quantum efficiency of >40% that produces a signal/noise ratio >3000 suffices for contemporary luminescent image capture and readily enables photometric analysis with a linear dynamic range of measure. An important practical limitation imposed by a lens with high numerical aperture is a small depth of focus that requires controlled flatness of the object plane. The plane of the object is consequently restricted in this system design by an optical platen (see FIG. 7C). Further, the reporting surface of the object is necessarily wet which offers the opportunity to optically couple the sample to the optical platen. Optically coupling the object to the system is essential to the intrascenic dynamic range of the measure (minimizing haze and other optical artifacts that detract from measuring bright and dim features within the same field of view).

The chief requirements of fluorescent imaging/detection are both efficient light detection and appropriate management of illumination. The design of efficient light detection discussed above (including optical coupling) delivers all of the essential capability to fluorescent imaging. Illumination management requires that excitation and emission light be discriminated. Design considerations for conditioning the wavelength of excitation light is discussed below (addressing absorption). Implicit to appropriate illumination management is the elimination of stray light, particularly that which emanates from materials that may fluoresce. Central to the design solution of this system is the minimization of excitation light from the productive path of emitted light (the acceptance cone of the lens system), as shown in FIG. 7A. This method of exciting fluorescence is traditionally recognized by those familiar with the art to be most effective; the method is generally called epi-illumination. Ideal epi-illumination of a flat surface (object plane) would involve illumination with parallel light 45 at a 45° angle of incidence (shown as "I" in FIG. 7A). In practice, an angle of incidence substantially less than 45° increases the possibility that excitation light from a normal reflection will enter the acceptance cone of the lens; sources of normal reflection include stray light from illumination and features in the field of view that deviate from the object plane. An example of a design using a small angle of incidence is that which uses "ring-light" illumination. Another constraint is that the angle of incidence must be less than about 60°, else an increasing amount of excitation light will not interact with the sample due to the total reflection caused by the critical angle of the platen (FIG. 7C). Any practical system of illumination will include light 60 that is not parallel. It is practical, indeed usual, to illuminate with light that is divergent as illustrated in FIG. 7B, where the illumination is shown as the finer lines entering from both sides of the object, a common method of epi-illumination used to enhance illumination uniformity. The illustration depicts slightly divergent light (about 18 degrees, or approximately f11), much less divergent than many commonly used methods such fiber illumination. The epi-illumination shown in FIG. 7B is preferred, since the extreme angles of incidence (and reflectance shown as bold lines) minimize the possibility of stray light entering the acceptance cone of the lens or critically reflecting from a planar surface.

A further important system design solution is embodied in FIG. 7C. The platen composition is a controlled optical surface, and as such may be constructed to minimize haze, autofluorescence and reflectance. Note that in this system design, the platen is the only material with which the excitation light has the opportunity to interact. Preferred composition of the platen is optical acrylic (UV transparent), whose sensor/illumination side is coated with an anti-reflective layer, and whose sample/object side is coated with an anti-abrasion layer (hard-coat). Other compositions (such as fused silica) are acceptable, but will manifest some performance decrement (transmit less light). As described above, the aqueous layer (ubiquitous to biological/biochemical systems) optically couples the sample surface to the platen and the object (the particle monolayer) is coated onto a flexible support having a mirror surface. The vast majority of the excitation light, which does not interact with the object particles, is simply reflected out of the system, away from the lens.

To summarize, in this preferred epi-illumination system for fluorescent excitation, the excitation light interacts only with a controlled optical component, a thin aqueous solution and a target particle before the light has a significant probability of entering the acceptance cone of the lens. Consequently, the lens system need only discriminate excitation from emitted light that emanates from the target particle. The discrimination of excitation from emitted light is commonly practiced in fluorescent imaging/detection, commonly using an interference filter (see filter 214—FIG. 7B). Such filters can be very costly and the capability of the filter to efficiently discriminate excitation and emitted light is often the chief limitation of detection sensitivity. In this preferred system design, the requirement of the filter to discriminate is reduced approximately 1000-fold compared to many fluorescent detection systems.

The chief requirements of absorption imaging/detection (generally called colorimetry) involve spectral resolution and photometry. The photometric precision of the system described above is more than 10-fold better than the basic system requirements for resolving thousands of "colors". The application requirement is similar to resolving/deconvoluting R, G, B and combinations/levels thereof. The fundamental method of color resolution involves measurement of the relative absorption characteristics of an object with differing wavelengths of light; the relative differences are tabulated to functionally define categories of dye combinations and levels. The dyes chosen must not interfere with other reporting optical elements, such as fluorochromes. One way to minimize anticipated interference is to choose "color" dyes whose absorbance spectrum is higher than any excitation/emission spectrum of the reporting fluorochromes.

Given a sufficient photometric precision, the number of colors that may be resolved (functionally defined) will depend upon the management of illumination and detection of light. Two fundamentally different methods of light management for the purpose of color resolution are either spectrally resolving "white" light before or after the light interacts with an object. The above system design requires that both methods be invoked for the sake of fluorescent imaging. The preferred design solution that is suitable for both absorption and fluorescent modes of imaging detection is to manage the spectral resolution of the illumination. Therefore, the illumination is managed by a light source and monochromater, having sufficient power and resolution to accommodate both modes of imaging. The solution is cost effective because the multi-filter design and implementation that would accommodate the excitation of multiple fluorescent probes and absorption of multiple colored dyes would easily exceed the cost of monochromator. Since the spectral excitation/absorption of the organic fluorochromes and dyes are relatively broad, a spectral resolution of only about 20 nm will suffice and the delivered illumination energy will be correspondingly higher than that associated with a "high resolution" monochromater (typically <2 nm). That the delivered energy will suffice for fluorescent imaging is assured by the sensitivity of the camera which is designed for luminescent imaging.

In the present method, a target analyte is suspended in solution with polymeric particles. The polymeric particles bear probes on their surface, which have an affinity for the target analyte. The target analyte associates with the probe on the surface of the particle. A recognition unit-peroxidase conjugate mareker is added to the suspension, which then associates with the target analyte already associated with the polymeric particle through the probe. The associated particle-target analyte-conjugate marker complex is allowed to settle onto a gelatin surface in contact with the suspension solution in the presence of a phenol. Hydrogen peroxide is then added to the mixture, resulting in attachment of the associated particle-target analyte-conjugate marker complex to the gelatin surface. Washing removes any unattached materials, and the remaining attached associated particle-target analyte-conjugate marker complex may be detected.

Figure 1A:
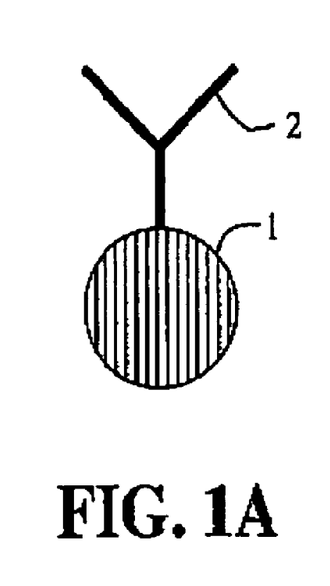
FIGS. 1A–1C are schematic diagrams illustrating the process of a target analyte molecule interacting with an antibody on the surface of a particle followed by the binding of a peroxidase conjugate marker.
Figure 1B:
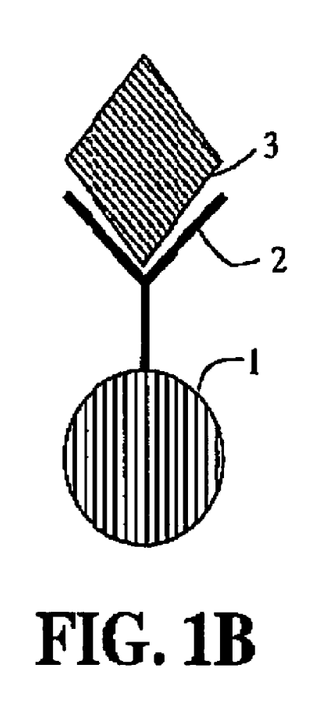
Figure 1C:
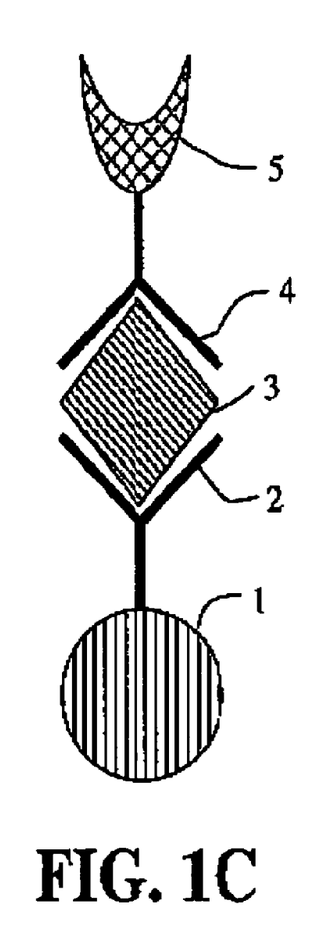
Figure 2A:
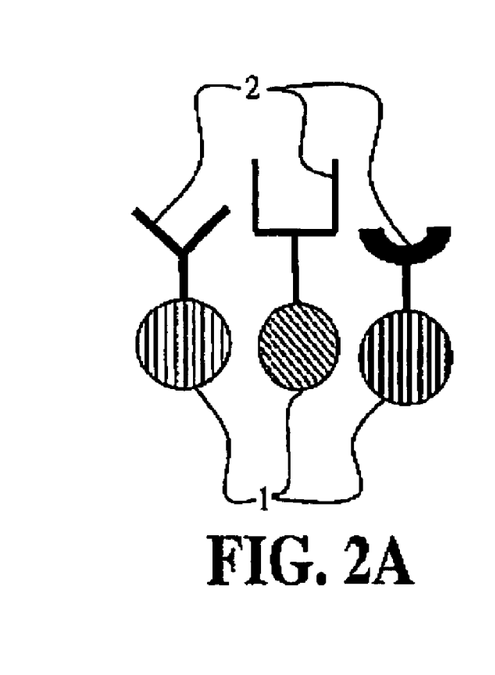
FIGS. 2A–2C are schematic diagrams illustrating the process of three types of target analyte molecules interacting with three different antibodies on the surface of three particles followed by the binding of three peroxidase conjugate markers to said analyte molecules.
Figure 2B:
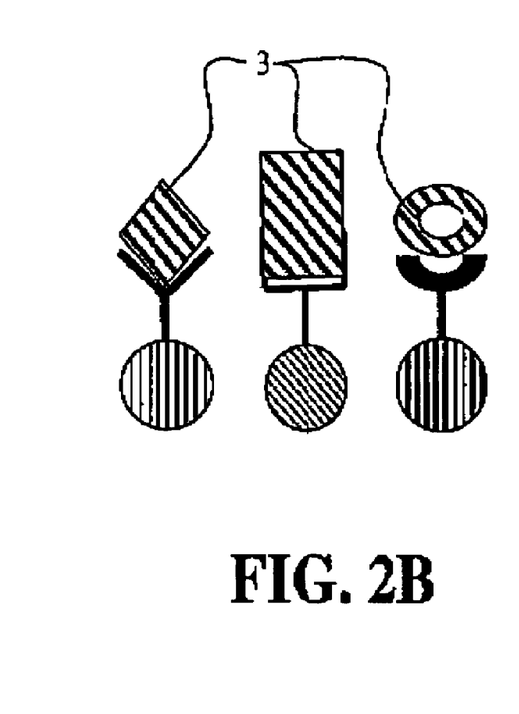
Figure 2C:
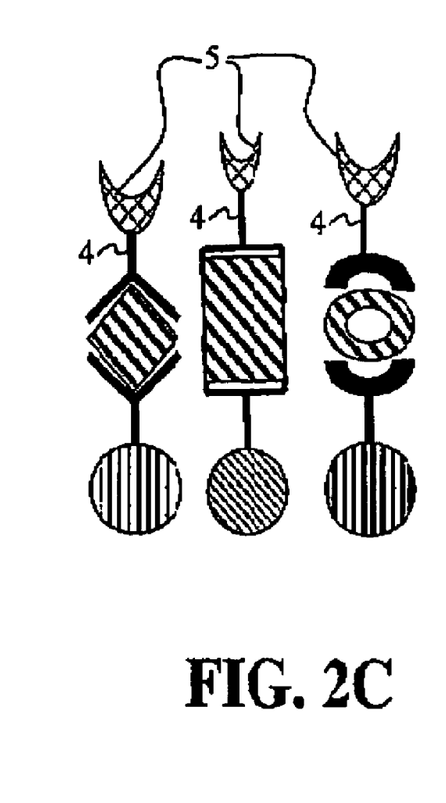

The invention is now described in reference to FIGS. 1–2, which are schematic diagrams illustrating the detection method of the invention in accordance with one preferred embodiment of the present invention. FIG. 1A shows schematically one preferred embodiment of the invention in which a particle 1 is modified on its surface with a probe 2, such as an antibody. Only one probe is shown in the figure, but more than one can be attached to the surface of the particle. In FIG. 1B a target analyte 3 to be identified is bound to probe 2 to form a complex on the surface of the particle 1. In FIG. 1C a conjugate marker consisting of an recognition unit 4, which may also be an antibody, conjugated to a peroxidase 5 is hybridized to target analyte 3. The particles having the probe-analyte-conjugate complex on their surfaces, as shown in FIG. 1C, are now ready to be spread onto a gelatin surface. FIG. 2A shows schematically another preferred embodiment of the invention in which three different particles, each one modified on its surface with a unique probe 2. Only one probe, for example, a protein capture agent, is shown in the figure, but more than one probe can be attached to the surface of the particle. FIG. 2B shows schematically the addition of three different target analytes to particle 1 with probe 2, and, subsequently, the formation of the probe-analyte-conjugate complex on the surfaces of each particle. In FIG. 2C, a conjugate marker consisting of a protein capture agent 4 and a peroxidase 5 is allowed to interact with the target analyte-probe-particle complex.

The process of spreading and adherence of particles shown in FIGS. 1C and 2C is schematically shown in FIG. 3A–D. FIG. 3A shows a support 1 coated with a layer of gelatin 2. The gelatin layer 2 has a surface 2A which is in contact with a fluid or liquid 3 which covers the surface 2A or a portion of the surface 2A. The surface 3A schematically represents the boundary or interface between the liquid 3 and the air or gas overlying the liquid 3. The particles 4 and 5 are immersed in or covered with a suitable suspending liquid 3 (it is noted that for the sake of clarity of illustration, only a part of the layer of liquid 3 is illustrated in FIGS. 3A–3D). The particles 4 and 5 may be brought in contact with the surface 2A of the gelatin layer 2 by covering the layer 2 with an amount of the liquid 3 in which the particles 4 and 5 are suspended or contained and allowing the particles 4 and 5 to sediment or settle to the surface 2A. Once the particles 4 and 5 have settled in the suspending liquid 3, the developer is added, resulting in the formation of a substance 6 that generates adhesive forces between the particle 4 and surface 2A (see FIG. 3B). The surface is then washed and detection and identification of the particle begun.

The invention can be better appreciated by reference to the following specific embodiments.

EXAMPLES

Preparation of Gelatin Coating

Solution A: 147.8 g of 35% gelatin solution, 963 g of water, 46.8 g of 9% siloxanes & silicones, di-Me, 2.5 g of 4.97% 1H-1,2,4-Triazolium, 1,4-diphnyl-3-(phenylamino)—inner salt, 3.55 g of 7.6% 2,4-Pentanediol, 2-methyl, and 36 g of 6.68% Ethanesulfonic acid, 2(2-(2-(4-(1,1,3,3-tetramethyl butyl) phenoxy) ethoxy)ethoxy)-, sodium salt.

Solution B: 106.2 g of 1.79% 1,1'-(methylene bis(sulfonyl) bis-ethene and 1,094 g of water.

Solution A and solution B were coated at 29.71 mL/square meter and 15.01 mL/square meter, respectively. The two solutions were delivered to and mixed at the coating hopper. The resulting coating was then dried. The coating contained 1.399 g of gelatin/square meter.

Experimental Protocol for Protein Detection (Mouse IgG):
Dye Incorporation into Polymeric Particles Three dyes used in this invention are dye1 and dye2 (MM2500FAN), and dye3 with their structures showed as follows:

Dye 1

Dye 2

Dye 3

A typical preparation of colored particles was by first dissolving appropriate amounts of individual dye 1–dye 3 or a mixture of dye 1–dye 3 in a toluene and acetone (ratio of toluene:acetone should be between 1:50 to 1:200) solution. A suspension of polystyrene particles with a diameter of approximately 10 micron was then added slowly (drop-wise) to this solution of the dyes while stirring to prepare a suspension of dye loaded particles. The suspension of colored particles was then poured into a dialysis bag (12,000 to 14,000 molecular weight cut off) and washed with running water for five hours.

Particle Modification

Spin down 500 µL of 10 µM carboxy modified polystyrene particles (1% w/w) in a 1.5 mL eppendorf tube for 3 minutes at 13000 RPM. Carefully remove supernatant and add 1 mL of 0.05 M acetate buffer, with 0.05% (w/w) Tween 20 pH 5.0. Vortex to homogenize. Repeat acetate buffer wash a second time and remove supernatant. Add 1 mL of the following solution: 0.1 M N-hydroxysuccinimide, (NHS) and 0.05 M 1-[3(dimethylamino)propyl]-3-ethylcarbodiimide hydrochloride (EDC) dissolved in 0.05 M acetate buffer. (115 mg NHS, 96 mg EDC, 10 mL acetate buffer). Vortex to homogenize and react for 1 hour at room temperature with agitation. Spin down particles for three minutes at 13000 RPM, remove supernatant and wash with acetate buffer, removing supernatant. Add 1 mL of a 1 mg/mL solution of antimouse IgG antibody in acetate buffer to particle pellet. Vortex to homogenize and react for 1 hour at room temperature with agitation. Wash particles three times in PBS buffer with 0.05% (w/w) Tween 20, pH 7.4.

Particle Attachment

Figure 4A:
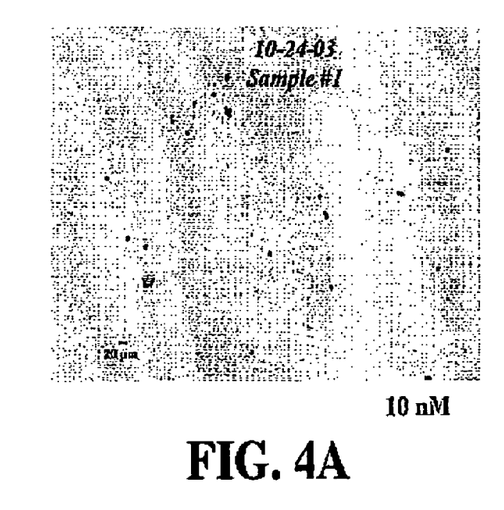
FIGS. 4A–4C show microscopic images of detecting $E.\ coli$ O157:H7 at three different concentrations by attaching particles to gelatin coated surface.
Figure 4B:
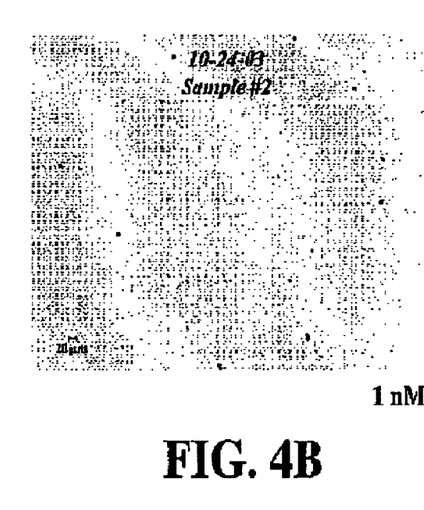
Figure 4C:
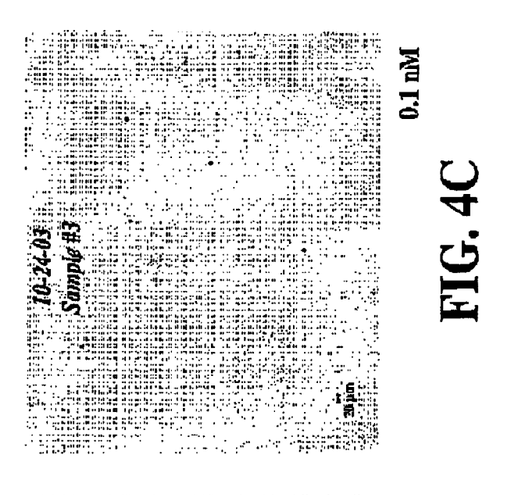

Invention: In a 1.5 mL eppendorf tube add 10 µL of 0.05% (w/w) antimouse modified particles and 990 µL of a 0.0001 mg/mL solution of Mouse IgG in PBS buffer. Incubate for one hour with agitation. Wash two times with PBS buffer w/0.05% Tween 20; remove supernatant. Add 1 mL of 0.001 mg/mL of Antimouse IgG-HRP in PBS buffer. Incubate for one hour at room temperature with agitation. Wash three times with PBS buffer w/0.05% Tween 20. Suspend particles in 1 mL of 0.05M Tris buffer pH 8.5 with 0.75 mg/mL p-coumaric acid, dispense over 25 mm×76 mm piece of gelatin coating and allow particles to settle for 5 min. Add 100 µL of 0.4% hydrogen peroxide to mixture and wait five minutes. Wash gelatin coating by pouring approximately 500 mL of distilled water over it. Observe under microscope (100× magnification). More than 95% particles are detected on the coating under microscopy (shown in FIGS. 4A–4C) that indicates the detection of target analytes.

Control: In a 1.5 mL eppendorf tube add 10 µL of 0.05% (w/w) antimouse modified particles and 990 mL of a PBS buffer. Incubate for one hour with agitation. Wash two times with PBS buffer w/0.05% Tween 20; remove supernatant. Add 1 mL of 0.001 mg/mL of Antimouse IgG-HRP in PBS buffer. Incubate for one hour at room temperature with agitation. Wash three times with PBS buffer w/0.05% Tween 20. Suspend particles in 1 mL of 0.05M Tris buffer pH 8.5 with 0.75 mg/mL p-coumaric acid, dispense over 25 mm×76 mm piece of gelatin coating and allow particles to settle for 5 min. Add 100 mL of 0.4% hydrogen peroxide to mixture and wait five minutes. Wash gelatin coating by pouring approximately 500 mL of distilled water over it. Observe under microscope (100× magnification). Less than 0.01% particles are detected on the coating under microscopy Experimental Protocol for Pathogen Detection (E. coli O157:H7):

Particle Modification

Spin down 500 µL of 10 µM carboxy modified polystyrene particles (1% w/w) in a 1.5 mL eppendorf tube for 3 minutes at 13000 RPM. Carefully remove supernatant and add 1 mL of 0.05 M acetate buffer, with 0.05% (w/w) Tween 20 pH 5.0. Vortex to homogenize. Repeat acetate buffer wash a second time and remove supernatant. Add 1 mL of the following solution: 0.1 M N-hydroxysuccinimide, (NHS) and 0.05 M 1-[3(dimethylamino)propyl]-3-ethylcarbodiimide hydrochloride (EDC) dissolved in 0.05 M acetate buffer. (115 mg NHS, 96 mg EDC, 10 mL acetate buffer). Vortex to homogenize and react for 1 hour at room temperature with agitation. Spin down particles for three minutes at 13000 RPM, remove supernatant and wash with acetate buffer, removing supernatant. Add 1 mL of a 1 mg/mL solution of affinity purified antibody to E. coli O157:H7 (Kirkegaard & Perry Laboratories, Inc., MD) (in acetate buffer to particle pellet. Vortex to homogenize and react for 1 hour at room temperature with agitation. Wash particles three times in PBS buffer with 0.05% (w/w) Tween 20, pH 7.4.

Particle Attachment

Figure 5A:
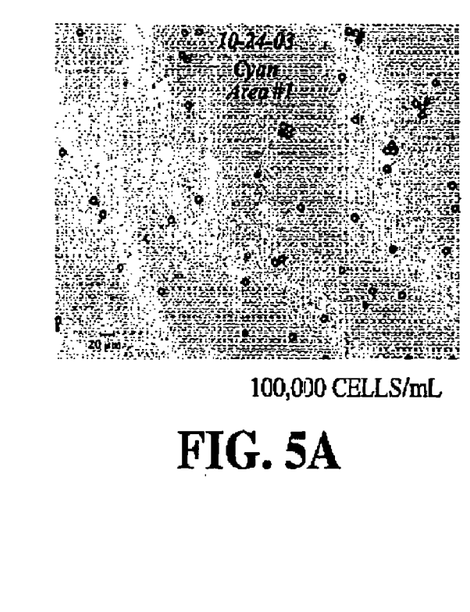
FIGS. 5A–5C show microscopic images of detecting a protein analyte molecule at three different concentrations by attaching particles to gelatin coated surface.
Figure 5B:
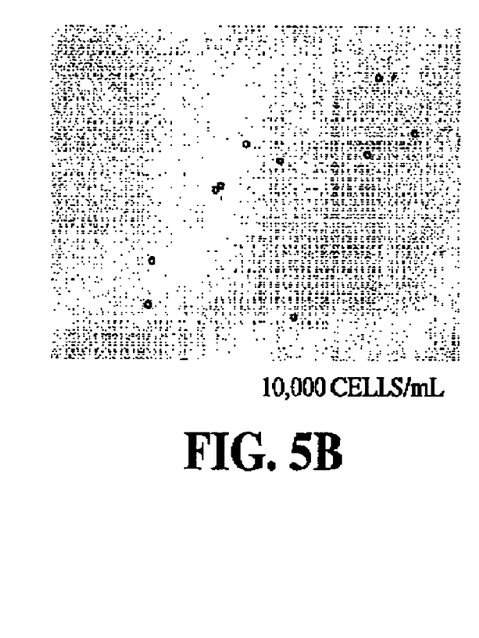
Figure 5C:
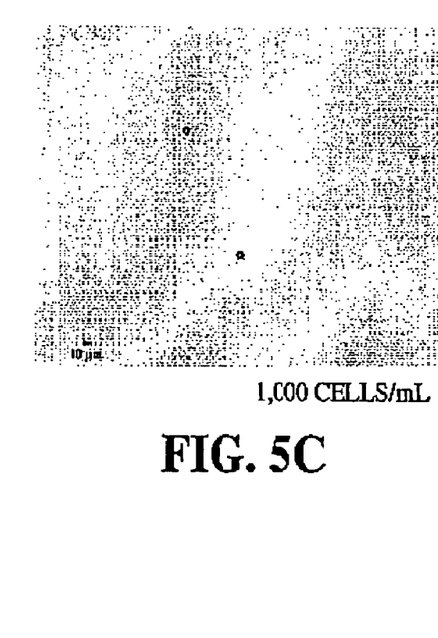

Invention: In a 1.5 mL eppendorf tube add 10 µL of 0.05% (w/w) anti-E. coli modified particles and 990 µL of E. coli O157:H7 (Kirkegaard & Perry Laboratories, Inc., MD) in PBS buffer with series of titer. Incubate for one hour with agitation. Wash two times with PBS buffer w/0.05% Tween 20; remove supernatant. Add 1 mL of 0.01 mg/mL of Anti E. coli-HRP (Kirkegaard & Perry Laboratories, Inc., MD) in PBS buffer. Incubate for one hour at room temperature with agitation. Wash three times with PBS buffer w/0.05% Tween 20. Suspend particles in 1 mL of 0.05M Tris buffer pH 8.5 with 0.75 mg/mL p-coumaric acid, dispense over 25 mm×76 mm piece of gelatin coating and allow particles to settle for 5 min. Add 100 µL of 0.4% hydrogen peroxide to mixture and wait five minutes. Wash gelatin coating by pouring approximately 500 mL of distilled water over it. Observe under microscope (100× magnification). More than 95% particles are attached to the coating (shown in FIGS. 5A–5C) that indicates the detection of target analytes.

Control: In a 1.5 mL eppendorf tube add 10 µL of 0.05% (w/w) anti-E. coli modified particles and 990 µL of a 0.0001 mg/mL solution of Salmonella (Kirkegaard & Perry Laboratories, Inc., MD) in PBS buffer. Incubate for one hour with agitation. Wash two times with PBS buffer w/0.05% Tween 20; remove supernatant. Add 1 mL of 0.01 mg/mL of Anti E. coli-HRP (Kirkegaard & Perry Laboratories, Inc., MD) in PBS buffer. Incubate for one hour at room temperature with agitation. Wash three times with PBS buffer w/0.05% Tween 20. Suspend particles in 1 mL of 0.05M Tris buffer pH 8.5 with 0.75 mg/mL p-coumaric acid, dispense over 25 mm×76 mm piece of gelatin coating and allow particles to settle for 5 min. Add 100 µL of 0.4% hydrogen peroxide to mixture and wait five minutes. Wash gelatin coating by pouring approximately 500 mL of distilled water over it. Observe under microscope (100× magnification). Less than 0.01% particles are attached to the coating.

Simultaneous Detection of a Protein Analyte and a Bacteria Analyte Using Different Color Coded Particles.

Figure 6A:
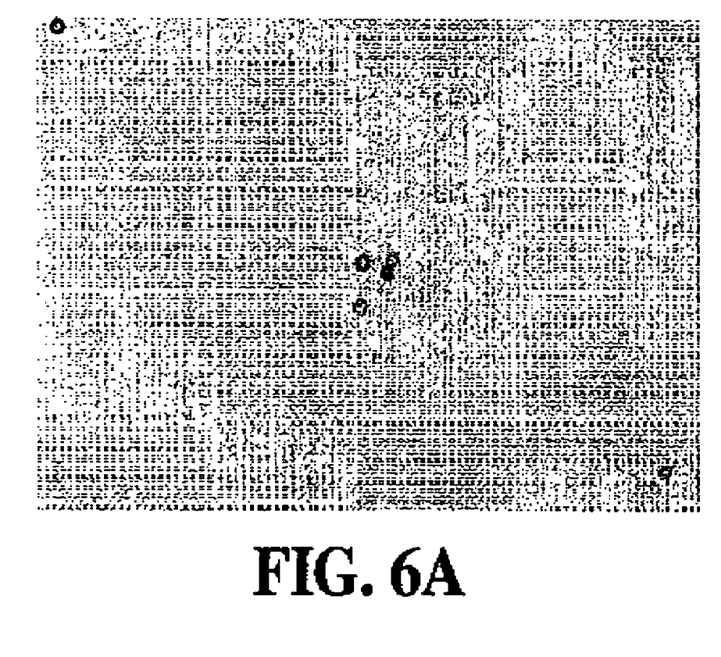
FIG. 6A shows a microscopic image of three different types of particles encoded with three colors.
Figure 6B:
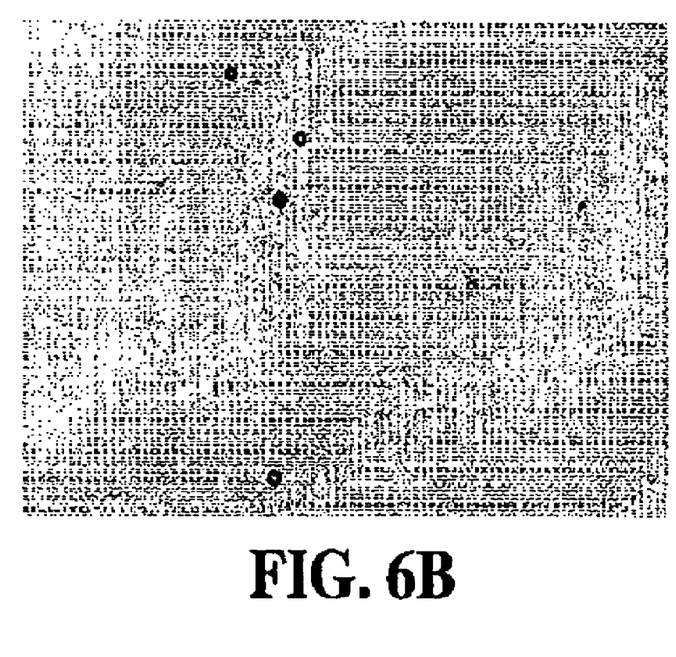
FIG. 6B shows a microscopic image of two different types of particles attached to gelatin coated surface for detecting two different analytes simultaneously.

Cyan colored particles are modified with anti-E. coli antibody on their surface as described above. Magenta colored particle are modified with anti-mouse IgG on their surface as described. Yellow particle were modified with BSA to serve as a control. To demonstrate the simultaneous detection of more than one analytes, the following step is performed in a test tube containing 10 µL of 0.02% Antimouse IgG modified magenta particles, 10 µL of 0.02% Anti-E coli modified cyan particles and 10 µL of 0.02% BSA modified yellow particles: added with 500 µL of a 0.001 mg/mL solution of Mouse IgG and 500 µL of a 0.001 mg/mL solution of E. coli both in PBS buffer with 0.05% Tween 20, incubate the solution mixture for one hour at room temperature with agitation, wash with PBS buffer w/0.05% Tween 20, incubate particles in 500 µL of a 0.01 mg/mL solution of anti-mouse IgG-HRP conjugate and 500 µL of a 0.01 mg/mL solution of anti-*E. coli*-HRP conjugate, both in PBS buffer with 0.05% Tween 20, incubate for one hour with agitation, wash particles 3 times with PBS buffer with 0.05% Tween 20, suspend particles in 1 mL of 0.05 M Tris buffer pH 8.5 with 0.75 mg/mL p-coumaric acid, dispense over 1"×3" piece of gelatin coating and allow particles to settle for 5 min, add 100 µL of 0.4% hydrogen peroxide to mixture and wait five minutes, wash gelatin coating by pouring approximately 500 mL of distilled water over it. The coating is observed under microscope (100× magnification.) as shown in FIG. 6A and FIG. 6B. The presence of cyan and magenta particles in FIG. 6B indicates the detection of protein analyte mouse IgG and bacteria analyte *E. coli*.

The invention has been described in detail with particular reference to certain preferred embodiments thereof, but it will be understood that variations and modifications can be effected within the spirit and scope of the invention.

The invention claimed is:

1. A method of detecting biological analytes comprising:
   suspending a target analyte in a suspending solution containing polymeric particles with an attached probe, wherein said probe has specific affinity for said target analyte;
   adding at least one recognition unit-peroxidase conjugate marker to said suspending solution, wherein said recognition unit associates with said target analyte;
   forming a complex of said target analyte, said polymeric particles with an attached probe, said recognition unit-peroxidase conjugate marker;
   contacting a gelatin surface with said suspending solution;
   adding developer to said suspending solution in contact with said gelatin surface in the presence of phenol to attach said complex to said gelatin surface;
   washing said gelatin surface; and
   detecting said complex attached to said gelatin surface.

2. The method of claim 1 wherein said target analyte is a protein.

3. The method of claim 1 wherein said target analyte is bacteria.

4. The method of claim 1 wherein said suspending solution is an aqueous solution.

5. The method of claim 4 wherein said suspending solution is buffered.

6. The method of claim 1 wherein said suspending solution further comprises phenol.

7. The method of claim 1 wherein said polymeric particles are organic.

8. The method of claim 1 wherein said polymeric particles are inorganic.

9. The method of claim 1 wherein said polymeric particles have a distinct color, shape or size.

10. The method of claim 9 wherein said shape is curvilinear, spherical, donut shaped, elliptical, rectangular, cubic, or rod.

11. The method of claim 9 wherein said color is derived from mixing three dyes representing the primary colors R, G, B to create distinct "color addresses."

12. The method of claim 11 wherein each of said distinct "color addresses" corresponds to a specific bioactive probe.

13. The method of claim 9 wherein said color is derived by covalently coupling one or more dyes to the surface of said polymeric particles.

14. The method of claim 9 wherein said color is derived from micro-encapsulated colorants and pigments incorporated into said polymeric particles.

15. The method of claim 1 wherein said polymeric particles are polystyrene, poly(methyl methacrylate) and poly(butyl acrylate).

16. The method of claim 1 wherein said polymeric particles have a mean diameter of from 1 to 100 microns.

17. The method of claim 1 wherein said polymeric particles have a mean diameter of from 2 to 30 microns.

18. The method of claim 1 wherein said polymeric particles have a mean diameter of front 3 to 20 microns.

19. The method of claim 1 wherein said polymeric particles are monodisperse wherein the coefficient of the particle size distribution (i.e. the standard deviation as a percentage of the mean) will be less than 20%.

20. The method of claim 1 wherein said polymeric particles are a plurality of particles types, wherein each type of particle is distinguishable from each other type of particle.

21. The method of claim 1 wherein said probe is a protein capture agent.

22. The method of claim 1 wherein said probe is an antibody.

23. The method of claim 1 wherein said probe has an affinity binding constant to said target analyte of greater than $10^6$ $M^{-1}$.

24. The method of claim 1 wherein said recognition unit is an antibody.

25. The method of claim 1 wherein said recognition unit has an affinity binding constant to the target analyte of no less than $10^6$ $M^{-1}$.

26. The method of claim 1 wherein said recognition unit is the same as said probe.

27. The method of claim 1 wherein said recognition unit is a nucleic acid.

28. The method of claim 1 wherein said peroxidase is connected to the recognition unit covalently.

29. The method of claim 1 wherein said peroxidase is connected to the recognition unit non-covalently.

30. The method of claim 1 wherein said peroxidase is horseradish peroxidase (HRP).

31. The method of claim 1 wherein said gelatin is coated onto a support.

32. The method of claim 31 wherein said support is organic, inorganic or biological.

33. The method of claim 31 wherein said support is glass, quartz, plastics, metals, semiconductors, a porous membrane.

34. The method of claim 1 wherein said gelatin further comprises hardener.

35. The method of claim 1 wherein said gelatin has a laydown of from 0.2 to 100 grams per square meter.

36. The method of claim 1 wherein said gelatin has a laydown of from 10 to 50 grams per square meter.

37. The method of claim 1 wherein said developer contains hydrogen peroxide.

38. The method of claim 1 wherein the concentration of said hydrogen peroxide in said developer is from 0.01% (w/v) to 10% (w/v).

39. The method of claim 1 wherein said developer is aqueous.

40. The method of claim 1 wherein said developer is buffered.

41. The method of claim 1 wherein said developer further comprises phenol.

42. The method of claim 1 wherein said phenol is added prior to or simultaneously with said developer.

43. The method of claim 1 wherein said phenol is represented by the following general formula:

where R1, R2, R3, R4, R5 are independently a hydrogen, a substituted or unsubstituted linear or branched alkyl group of 1 to 10 carbon atoms, a substituted or unsubstituted aryl group of 6 to 14 carbon atoms, a substituted or unsubstituted cycloalkyl group of 5 to 14 carbon atoms, a substituted or unsubstituted heterocyclic group, a solubilizing group, or a halogen atom of fluoride, chloride, bromide, iodide.

44. The method of claim 43 wherein at least one of R1, R2, R3, R4, R5 is or contains a solubilizing substituent that is generally negatively charged.

45. The method of claim 1 wherein said phenol is represented by at least one of the following structures:

46. The method of claim 1 wherein said washing is aqueous.

47. The method of claim 1 wherein said detecting is visual inspecting.

48. The method of claim 47 wherein said visual inspecting utilizes a microscope.

49. The method of claim 1 wherein said detecting is automatic imaging.

50. The method of claim 1 wherein said detecting is dark field illumination epi-illumination, phase-contrast microscopy, differential interference contrast microscopy (DIC), polarization microscopy, multi-spectral or hyper-spectral microscopy.

51. The method of claim 1 wherein said detecting is full-frame image capture.

* * * * *